US009119679B2

(12) United States Patent
Ralph et al.

(10) Patent No.: US 9,119,679 B2
(45) Date of Patent: *Sep. 1, 2015

(54) ANGLED WASHER POLYAXIAL CONNECTION FOR DYNAMIC SPINE PROSTHESIS

(71) Applicant: GMEDELAWARE 2 LLC, Audubon, PA (US)

(72) Inventors: Christopher R. Ralph, Woodinville, WA (US); Cin Kiat Abidin, Issaquah, WA (US); Devin Lee Joseph Looijen, Carnation, WA (US); Matthew M Quest, Bothell, WA (US); Philip Tracy Berg, Federal Way, WA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/198,168

(22) Filed: Mar. 5, 2014

(65) Prior Publication Data
US 2014/0303671 A1 Oct. 9, 2014

Related U.S. Application Data

(63) Continuation of application No. 11/837,335, filed on Aug. 10, 2007, now Pat. No. 8,702,755.

(60) Provisional application No. 60/837,458, filed on Aug. 11, 2006.

(51) Int. Cl.
*A61B 17/70* (2006.01)
*A61F 2/44* (2006.01)
*A61B 17/86* (2006.01)
*A61F 2/30* (2006.01)

(52) U.S. Cl.
CPC .......... *A61B 17/7064* (2013.01); *A61F 2/4405* (2013.01); *A61B 17/86* (2013.01); *A61F 2002/3055* (2013.01); *A61F 2002/30462* (2013.01); *A61F 2002/30507* (2013.01); *A61F 2002/30538* (2013.01); *A61F 2002/30563* (2013.01); *A61F 2002/30616* (2013.01); *A61F 2220/0025* (2013.01); *A61F 2220/0075* (2013.01); *A61F 2250/0006* (2013.01); *A61F 2250/0007* (2013.01)

(58) Field of Classification Search
CPC ... A61B 17/7064; A61B 17/86; A61F 2/4405
USPC ............................. 606/60, 70, 71, 246–331; 623/17.11–17.16
See application file for complete search history.

(56) References Cited

U.S. PATENT DOCUMENTS 5,312,404 A * 5/1994 Asher et al. .................. 606/264
5,984,924 A * 11/1999 Asher et al. .................. 606/264
(Continued)

Primary Examiner — Christopher Beccia

(57) ABSTRACT

A dynamic spine prosthesis (such as a facet joint prosthesis having an articulation surface configured to articulate with a corresponding facet joint element) that has a fixation element with an elongated bone entry portion defining a longitudinal axis and a dynamic spine prosthesis component connected to the fixation element at a connection location by an adjustable connection. The adjustable connection has first and second washers each rotatably supported by the fixation element and each having an angled contact surface in a plane not perpendicular to the longitudinal axis of the fixation element, with the connection location being between the bone entry portion and the first and second washers.

15 Claims, 5 Drawing Sheets

(56) References Cited

U.S. PATENT DOCUMENTS

| | | | |
|---|---|---|---|
| 6,669,697 B1 * | 12/2003 | Pisharodi | 606/264 |
| 7,608,104 B2 * | 10/2009 | Yuan et al. | 623/17.11 |
| 7,766,943 B1 * | 8/2010 | Fallin et al. | 606/264 |
| 8,702,755 B2 * | 4/2014 | Ralph et al. | 606/246 |
| 2005/0234459 A1 * | 10/2005 | Falahee et al. | 606/72 |
| 2006/0007562 A1 * | 1/2006 | Willey et al. | 359/811 |
| 2006/0271046 A1 * | 11/2006 | Kwak et al. | 606/61 |

* cited by examiner

ANGLED WASHER POLYAXIAL CONNECTION FOR DYNAMIC SPINE PROSTHESIS

CROSS REFERENCE TO RELATED APPLICATIONS

This application is a continuation application of U.S. patent application Ser. No. 11/837,335 which claims the benefit of U.S. Provisional Application No. 60/837,458 filed Aug. 11, 2006, which are is incorporated by reference as if fully set forth herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

The invention relates generally to dynamic spine prostheses. In particular, the invention relates to dynamic spine prostheses with components whose position with respect to a spine fixation element may be adjusted.

There are multiple types of spine modification devices that may be implanted by attachment to one or more vertebrae to treat a variety of disorders. For example, spinal fusion systems fix the spatial relationships between two or more vertebrae. One such system is described in U.S. Pat. No. 6,080, 156. Fusion systems, such as the one shown in the '156 patent, are typically attached to the vertebrae by screws placed in the pedicle. Because all components of such fusion systems are essentially immobile with respect to each other, each component must continually bear and transmit to adjacent components all forces exerted on the device anywhere in the device until the treated vertebral bodies have fused, at which point the bony fusion generally absorbs the majority of the intervertebral loads. Because such fusion devices are typically utilized in conjunction with other fusion-promoting techniques and tools, such as disc evacuation and packing with bone graft, the use of interbody fusion cages and bone graft, gutter grafting and/or the use of BMP or other arthrodesis promoting tools and techniques, it is generally only necessary for such fusion devices to function for a limited amount of time before the arthrodesis assumes the majority of the vertebral loading.

Unlike fusion systems, however, dynamic spine prostheses attach to two or more vertebrae and have components that move with respect to each other as the vertebrae to which they are attached move. Moreover, dynamic spine prostheses should be designed to assume normal physiological loading (as well as transient excessive loading conditions) for the lifetime of the patient, which could easily exceed 10,000,000 cycles or more. Dynamic spine prostheses can include artificial facet joint prostheses (such as, e.g., the Total Facet Arthroplasty System® available from Archus Orthopedics, Inc., the AFRS system available from Facet Solutions, and the TOPS system available from Impliant, Ltd.) as well as dynamic stabilization systems (such as, e.g., the Stabilimax NZ system available from Applied Spine Technologies, the Axient system available from Innovative Spinal Technologies, the N-Flex system available from N-Spine, and the Accuflex system available from Globus Medical.) and dynamic interspinous-spacer systems (such as, e.g., the X-Stop system available from Kyphon/St. Francis Medical Technologies, the Coflex system available from Paradigm Spine, the Extensure system available from Nuvasive, and the Wallis system available from Abbott Spine.).

SUMMARY OF THE INVENTION

Due to patient to patient differences in spinal anatomy as well as to anatomical changes caused by a particular patient's disease state, the relationship between the fixation elements (such as screws, posts, etc.) of a dynamic spine prosthesis to the remaining components of the prosthesis may vary from patient to patient and from disease state to disease state. However, unlike spinal fusion prosthesis, the connections between the fixation elements and the dynamic (or motion-allowing) elements of a dynamic spine prosthesis must be capable of withstanding repetitive loading (both normal physiological loading as well as transient excessive loading) for the remaining lifetime of the patient. The invention therefore provides an adjustable connection between a dynamic spine prosthesis fixation element and other components of the prosthesis which is capable of withstanding such loading for an extended period of time, up to, and including, the lifetime of the patient and/or the implant. Moreover, because physicians will also often desire the fixation elements to be placed in a desired location and/or orientation relative to the surrounding anatomical structures (such as to increase the strength of the of the fixation by maximizing cortical bone purchase and/or to accommodate unusual or size-constrained anatomical features), and such positioning is often non-optimal for the placement of the dynamic elements of the device, the present invention allows the physician to place the fixation elements in virtually any orientation or position, and then securely fix the properly-functioning implant relative to the location and/or orientation of the fixation members.

The invention relates generally to implantable devices, apparatus or mechanisms that are suitable for implantation within a human body to restore, augment, and/or replace hard tissue, soft tissue and/or connective tissue, including bone and cartilage, and systems for treating the anatomic or functional manifestation of injury or diseases, such as spinal pathologies. In some instances, the implantable devices can include devices designed to replace missing, removed, or resected body parts or structure. The implantable devices, apparatus or mechanisms are configured such that the devices can be formed from parts, elements or components which alone or in combination comprise the device. The implantable devices can also be configured such that one or more elements or components are formed integrally to achieve a desired physiological, operational or functional result such that the components complete the device. Functional results can include the surgical restoration and functional power of a joint, controlling, limiting or altering the functional power of a joint, and/or eliminating the functional power of a joint by preventing joint motion. Portions of the device can be configured to replace or augment existing anatomy and/or implanted devices, and/or be used in combination with resection or removal of existing anatomical structure.

One aspect of the invention provides a dynamic spine prosthesis (such as, for example, a facet joint prosthesis having an articulation surface configured to articulate with a corresponding facet joint element) that has a fixation element with an elongated bone entry portion defining a longitudinal axis and a dynamic spine prosthesis component connected to the fixation element at a connection location by an adjustable connection. The adjustable connection has first and second washers each rotatably supported by the fixation element and each having an angled contact surface in a plane not perpendicular to the longitudinal axis of the fixation element, with the connection location being between the bone entry portion and the first and second washers.

In some embodiments, the angled contact surfaces of the first and second washers are in contact with each other. There also may be a third washer between the dynamic spine prosthesis connection location and the bone entry portion, with the third washer comprising a partial spherical surface.

In some embodiments, the dynamic spine prosthesis also has a tightening element (such as, e.g., a compression nut) having a first position enabling movement between the first and second washers and the fixation element and a second position preventing movement between the washers and the fixation element.

In some embodiments, the adjustable connection also has a structural attachment element supporting the dynamic spine prosthesis component, with the structural attachment element having a first position in which the dynamic spine prosthesis component is movable with respect to the structural element and a second position in which the dynamic spine prosthesis component is fixed with respect to the structural element.

Another aspect of the invention provides a method of adjusting a position of a component of a dynamic spine prosthesis (such as a facet joint prosthesis having an articulation surface configured to articulate with a corresponding facet joint element) with respect to a bone fixation element supporting the dynamic spine prosthesis. The method includes the steps of inserting a bone entry portion of the fixation element into a vertebra; moving the dynamic spine prosthesis component to a desired position with respect to a connection location between the dynamic spine prosthesis component and the fixation element, the connection location being between the bone entry portion and first and second washers, the first and second washers each having an angled contact surface in a plane not perpendicular to a longitudinal axis of the fixation element and being supported by the fixation element; rotating the first washer with respect to the second washer; and immobilizing the washers and the dynamic spine prosthesis component with respect to the fixation element.

In some embodiments, the method includes the step of rotating the second washer with respect to the fixation element.

In some embodiments, the step of moving the dynamic spine prosthesis component includes the step of moving the dynamic spine prosthesis component with respect to a support disposed at the connection location. In some embodiments, the immobilizing step may include the step of immobilizing the dynamic spine prosthesis component with respect to the support, such as by tightening a compression nut threadably mounted on an extension of the fixation element.

BRIEF DESCRIPTION OF DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which.

DETAILED DESCRIPTION OF THE INVENTION

Figure 1:
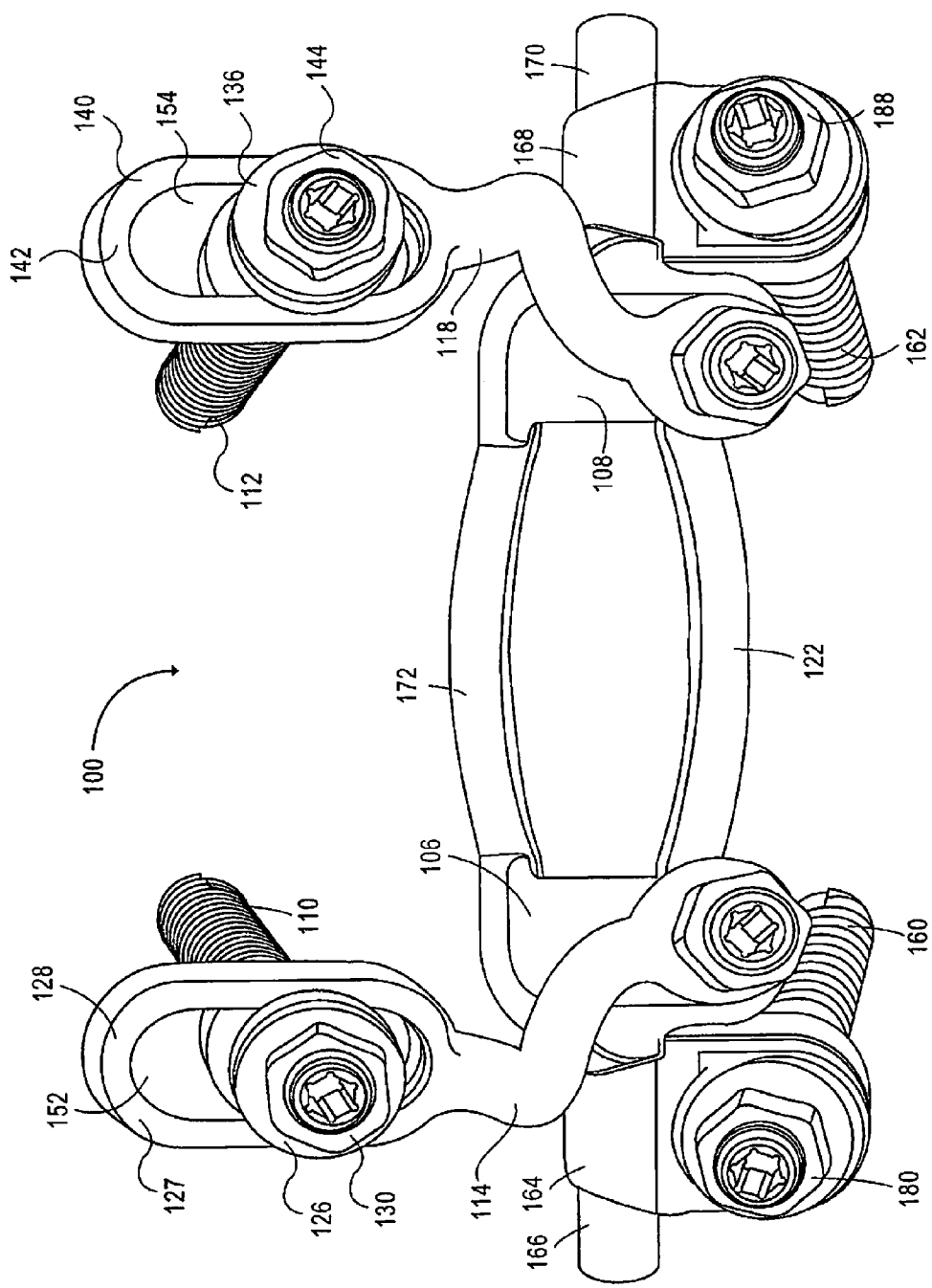
FIG. 1 is front elevational view of a dynamic spine prosthesis according to one embodiment of the invention.
Figure 2:
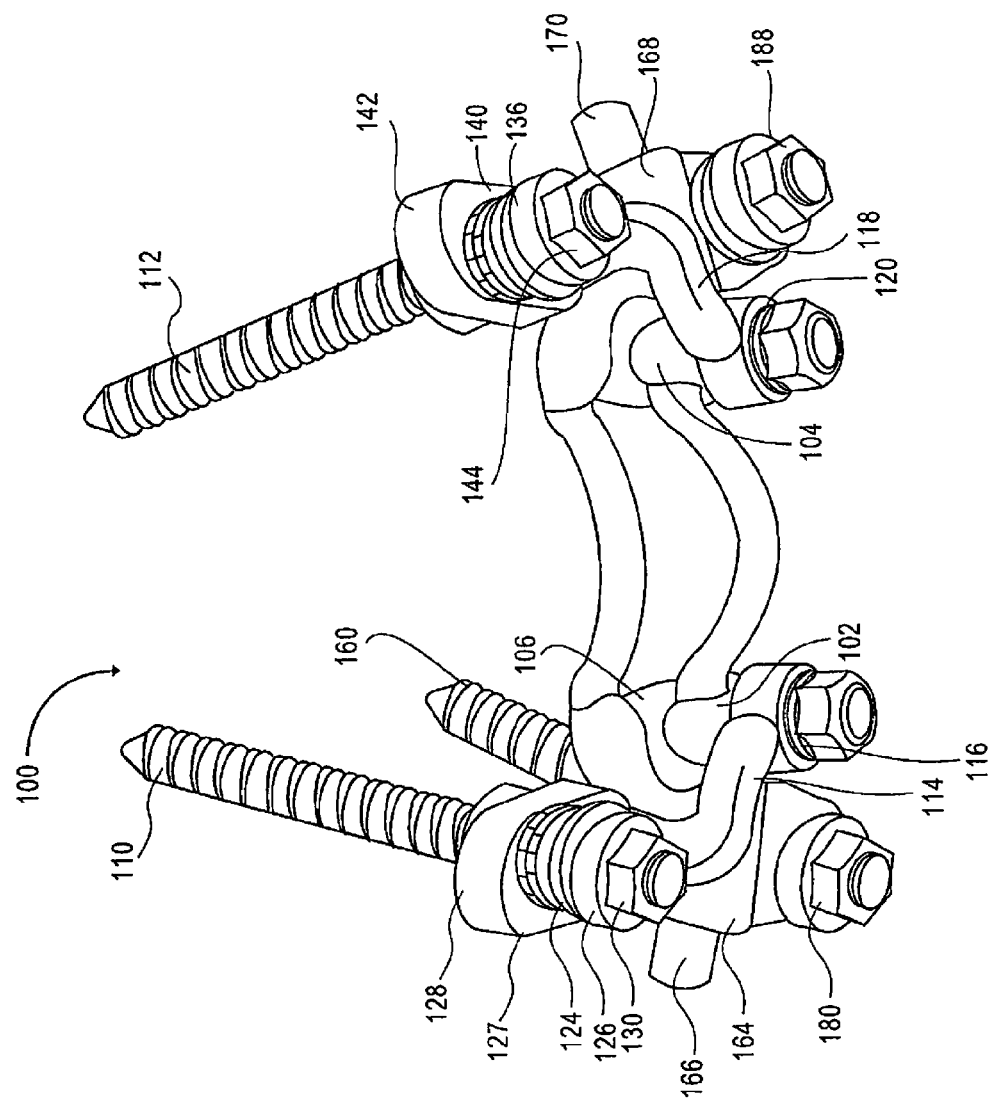
FIG. 2 is a perspective view of the dynamic spine prosthesis of FIG. 1.
Figure 3:
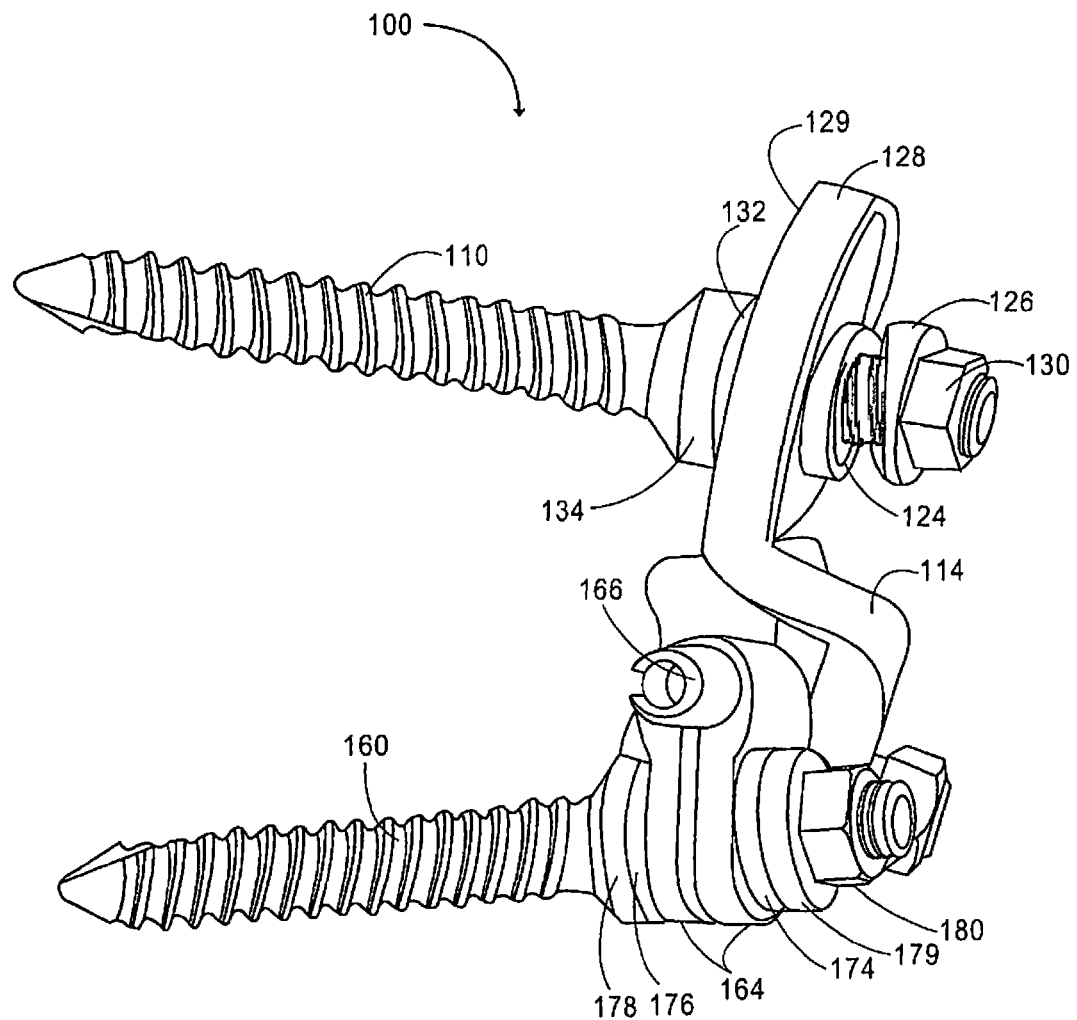
FIG. 3 is a right side elevational view of the dynamic spine prosthesis of FIG. 1.
Figure 4:
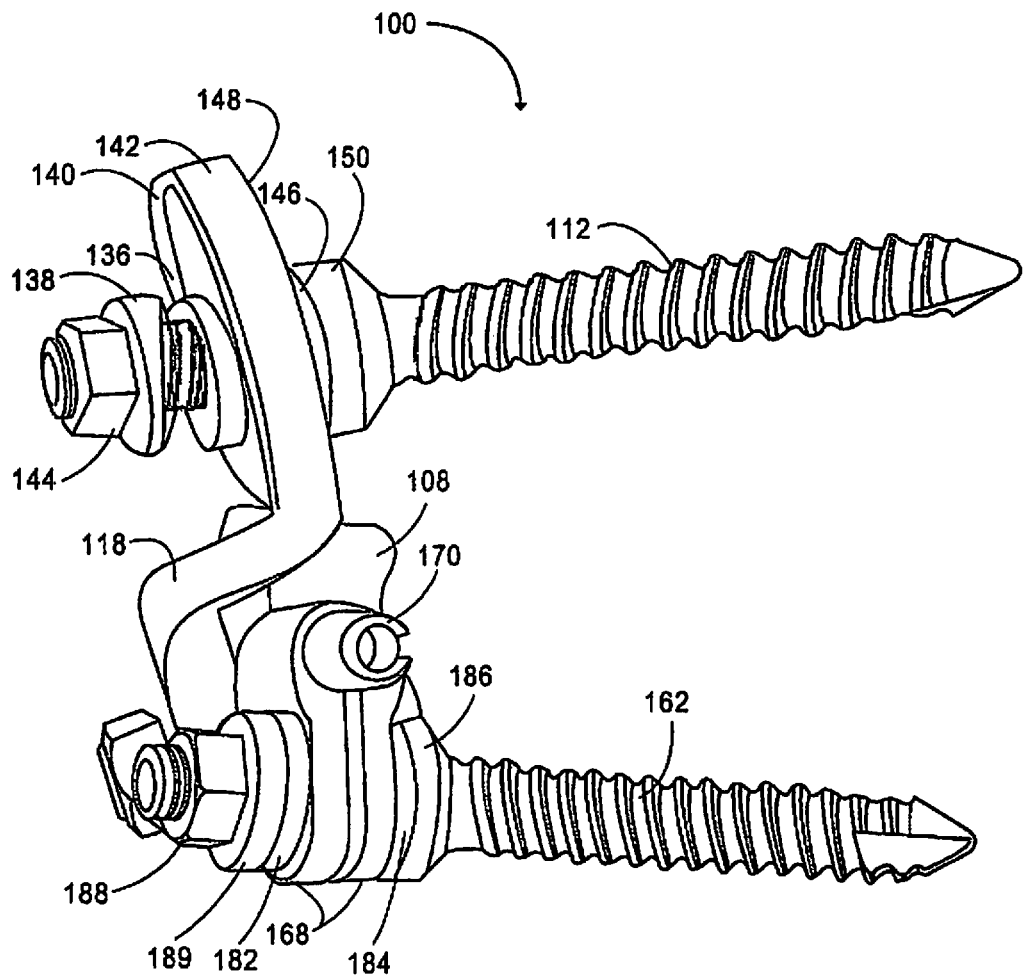
FIG. 4 is a left side elevational view of the dynamic spine prosthesis of FIG. 1.
Figure 5:
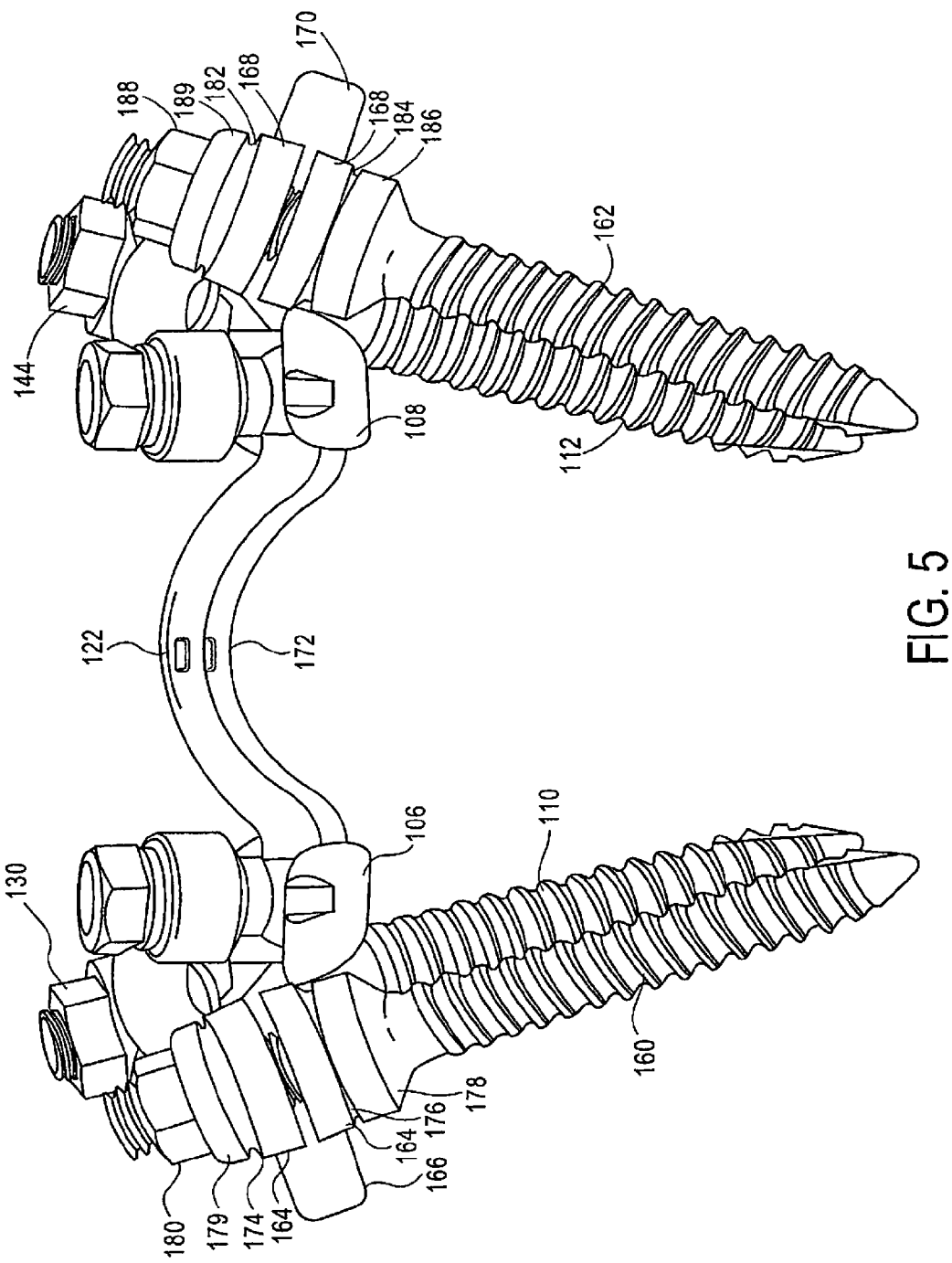
FIG. 5 is a bottom elevational view of the dynamic spine prosthesis of FIG. 1.

FIGS. 1-5 show one embodiment of a dynamic spine prosthesis according to this invention. In this embodiment, the dynamic spine prosthesis is an artificial facet joint prosthesis 100 providing left and right cephalad facet joint bearing elements 102 and 104 and left and right caudal facet joint bearing elements 106 and 108, respectively. When the cephalad facet joint bearing elements are attached to a superior vertebra and the caudal facet joint bearing elements are attached to an inferior vertebra, the corresponding left and right bearing elements move with respect to each other and bear against each other as the patient moves his or her back, which is often a combination of one of more of the following motions: flexion, extension, rotation and/or lateral bending.

The cephalad facet joint bearing elements attach to a superior vertebra via fixation elements, such as screws 110 and 112 having threaded bone entry portions. A left arm 114 extends generally downward from fixation element 110 to a support bar 116 to which left cephalad bearing element 102 is attached. Likewise, a right arm 118 extends generally downward from fixation element 112 to a support bar 120 to which right cephalad bearing element 104 is attached. A crossbar 122 extends between the right and left cephalad bearing elements.

Because of differences in patient anatomy, the cephalad portion of the dynamic spine prosthesis has adjustment mechanisms for adjusting the spatial relationship between the fixation elements and the other prosthesis components. First, the angle between the left cephalad fixation element 110 and the left support arm 114 may be adjusted and fixed in the adjusted position by rotating two angled washers 124 and 126 mounted on a proximal extension of fixation element 110 between the proximal face 127 of a fixation region 128 on the top end of arm 114 and a compression nut 130 or other tightening element. Because each washer 124 and 126 has a contact surface not perpendicular to the axis of fixation element 110, each washer 124 and 126 may be rotated about fixation element 110 to change the angle between arm 114 (and, therefore, cephalad bearing element 102) and fixation element 110. When the proper orientation has been set, tightening element 130 is tightened along a threaded proximal extension of fixation element 110 to keep the components in place.

In this embodiment, a partially spherical washer 132 is disposed between the distal face 129 of the left cephalad support arm's fixation region 128 rests in an annular channel 134 on fixation element 110 to provide firm contact between the distal face of the arm fixation region and the fixation element. Alternatively, a second pair of angled washers may be used in place of the partially spherical washer.

Similarly, the angle between the right cephalad fixation element 112 and the right support arm 118 may be adjusted and fixed in the adjusted position by rotating two angled washers 136 and 138 mounted on a proximal extension of fixation element 112 between the proximal face 140 of a fixation region 142 on the top end of arm 114 and a compression nut 144 or other tightening element. As on the left side, because each washer 136 and 138 has a contact surface not perpendicular to the axis of fixation element 112, each washer 136 and 138 may be rotated about fixation element 112 to change the angle between arm 118 (and, therefore, cephalad bearing element 104) and fixation element 112. When the proper orientation has been set, tightening element 144 is tightened along a threaded proximal extension of fixation element 112 to keep the components in place.

As on the left side, in this embodiment a partially spherical washer 146 disposed between the distal face 148 of the right cephalad support arm's fixation region 142 rests in an annular channel 150 on fixation element 112 to provide firm contact between the distal face of the arm fixation region and the fixation element. Once again, a second pair of angled washers may be used in place of the partially spherical washer.

An additional adjustment mechanism is provided by the oval shaped openings 152 and 154 of the fixation regions 128 and 142 of left and right cephalad support arms 114 and 118, respectively. The support arms 114 and 118 may be moved up or down with respect to fixation elements 110 and 112, respectively, before tightening compression screws 130 or 144 to further adjust the spatial relationships between cephalad facet bearing elements 102 and 104 and fixation elements 110 and 112. The cephalad support arms 114 and 118 may also be rotated about their respective fixation elements 110 and 112 before tightening.

The caudal facet joint prosthesis components may be adjusted with respect to their fixation elements as well. The caudal facet prosthesis bearing elements attach via screws or other fixation elements 160 and 162 to a vertebra inferior to the vertebra to which the cephalad components have been attached. Looking first on the left side, a clamp 164 mounted on fixation element 160 holds a left caudal support bar 166 extending from left caudal bearing surface 106. Likewise, a clamp 168 mounted on fixation element 162 holds a right caudal support bar 170 extending from right caudal bearing surface 108. A crossbar 172 extends between the left and right caudal bearing surfaces.

In this embodiment, the angle between the left caudal fixation element 160 and the left caudal clamp 164 may be adjusted by rotating a first partially spherical washer 174 (disposed proximal to clamp 464) with respect to a cap 179 beneath a compression screw 180 and/or by rotating a second partially spherical washer 176 (disposed distal to clamp 164) with respect to an annular channel 178 formed in fixation element 160. When the proper orientation has been achieved, compression screw 180 or other tightening element is tightened along a threaded proximal extension of fixation element 160 to fix these components in place. Alternatively, a pair of angled washers may be used in place of the partially spherical washers, as in the cephalad component. Likewise on the right side, the angle between the right caudal fixation element 162 and the right caudal clamp 168 may be adjusted by rotating a first partially spherical washer 182 (disposed proximal to clamp 168) with respect to a cap 189 beneath a compression screw 188 and/or by rotating a second partially spherical washer 184 (disposed distal to clamp 168) with respect to an annular channel 186 formed in fixation element 162. When the proper orientation has been achieved, compression screw 188 or other tightening element is tightened along a threaded proximal extension of fixation element 162 to fix these components in place. Alternatively, a pair of angled washers may be used in place of the partially spherical washers, as in the cephalad component, as before.

Because the various components of the present invention allows for significant adjustment and/or modular variability between the dynamic elements and the fixation elements, the device is particularly well suited for use in virtually all levels of the spine, and for virtually all anatomical variations, including adult males or females or even children. If desired, the fixation elements can incorporate bony in-growth and/or osteo-integration surfaces and/or materials, or the various fixation elements could be utilizes in conjunction with auxiliary fixation materials such as ceramic, crystalline, organic, polymeric or other types of bone cement or adhesives. Where the device fails for some reason, or revision is necessitated (such as, for example, where a young patient "grows out of" the device), a physician could access the device and disassemble those pieces necessary to be replaced, and then reassemble the same or a different size or configuration of the device, or assemble a fusion construct utilizing one or more of the original fixation elements already integrated within and/or attached to the patient's bones.

If desired, the devices of the present invention could be utilized with virtually any dynamic system, including those used in combination with an artificial spinal disc replacement device. Virtually all of the various embodiments disclosed here could be utilized, in various ways, in combination with artificial disc replacement devices, as well as nucleus repair systems and replacement devices, interbody spacers, dynamic stabilization devices, articulating rod and screw systems, posterior ligament or annular repair and/or augmentation devices, interspinous spacers, facet replacement and/or resurfacing devices, and the like. Use of the present devices in a dynamic system, in combination with an artificial disc replacement or repair, provides a solution for the total disc replacement contraindication of facet degeneration. Moreover, implantation of a total disc replacement device after removal of some or all of one or more of the facets and/or other intervening tissues (hard or soft), but prior to implantation of the dynamic device, provides a large, safe and repeatable access to the disc space, as well as aiding in any decompression of the joint that may be necessary. Such access facilitates passage of one or more components of the artificial disc replacement (or nucleus replacement, or annular repair material, and their respective tools) through the removed facet tissues via a lateral, posterior-lateral and/or posterior approach. The functions of the removed tissues can then be replaced by implanting the dynamic device as described herein. Of course, the dynamic devices disclosed herein (and the surgical removal of tissues to create one or more access paths) may be used unilaterally or bilaterally, depending on the nature of and stage of disease, and can be used at multiple levels of the spine of facet and/or other intervening tissues.

In various embodiments, a series of artificial dynamic components of differing shapes, sizes and/or orientations and/or lengths can be provided to accommodate different objectives, including alteration of dynamic element height/orientation relative to the fixation element, to accommodate different loading conditions due to other surgical treatments (i.e., artificial disc replacement of the same or other spinal level, annular repair, nucleus replacement, dynamic stabilization, interspinous spacer and/or adjacent level fusion and/or facet replacement devices). Moreover, to accommodate differing designs (i.e., constrained discs versus unconstrained discs) and/or arrangement/positioning of artificial disc replacement devices used on the same or different spinal levels, the dynamic elements could be of differing shapes, sizes, orientations and/or lengths to accommodate the different loading profiles induced or desired by the artificial disc replacement devices.

In one alternate embodiment, once the components of the device have been secured to the targeted vertebral bodies, one or more elastic compression devices or "bands" could be secured about the dynamic elements (or to the vertebral bodies themselves, or between other parts of the device, or any combination thereof). Properly positioned and/or tensioned, these "bands" would tend to keep the dynamic elements in contact and/or close proximity, even under extreme and/or unusual loading conditions, and thus reduce and/or eliminate the opportunity for the device to dislocate. Moreover, in the event that dislocation of the device did occur, the bands could prevent and/or limit motion of the dislocated joint (by holding the dynamic elements together), and thus reduce or eliminate damage to other tissues (such as the spinal cord, various other nerves and/or circulatory/connective tissues) resulting from the dislocation. In fact, the compression of the bands might make it possible to eventually "reduce" the dislocation and/or repair the dislocated device through external manipulation and/or minimally-invasive surgery. If desired, one or more "bands" could be secured between the dynamic elements of the device, or between the various surfaces, arms, cups, stems and/or cross-arms of the device components, with varying results.

In another alternative embodiment, the compression device could comprise an elastic or pliable material surrounded by a non-elastic housing, whereby the elastic material allows various movement of the dynamic elements (with resistance commensurate to the flexibility of the material), but the non-elastic housing acts as an ultimate "stop" to movement of the dynamic elements beyond a certain predetermined limit. Similarly, the "band" could comprise an elastic, non-elastic or rigid material, such as stainless steel cable, which desirably prevents relative motion of the elements of the device beyond a certain pre-defined maximum extension/flexion.

Advantageously and in contrast to conventional techniques where fusion and dynamic implants are implanted via an open procedure, a majority of the components of the present dynamic devices can be surgically implanted using minimally-invasive techniques alone or in combination with conventional open techniques. For example, all or most of the components of the device may be delivered through a cannula inserted through a small incision in the skin. To implant the device components, the physician can first create an access path through the skin and soft tissue (with a spinal needle and/or K-wire) to the targeted vertebral body. Desirably, non-invasive visualization, such as fluoroscopic or real-time MRI, is used to monitor the advancement of the needle and avoid damage to tissue structures such as muscles, tendons, ligaments, nerves, veins and/or the spinal cord itself. Once the access path has been created, a suitable cannula can be advanced through the tissues to the targeted bone. If necessary, progressively larger dilation catheters (such as the Access™ Dilation Port commercially available from Spinal Concepts of Austin, Tex.) can be used to introduce a cannula having a lumen large enough to accommodate passage of the components.

Depending upon the patient's condition and the desired surgical outcome, as well as the surgeon's preference, the present embodiment can facilitate the repair and replacement/augmentation of the facet joints in a minimally-invasive, limited-open (or modified-open) and/or fully-open surgical procedure. For example, where facet joint replacement is deemed necessary, but removal of soft and/or hard tissues in and/or adjacent the spinal canal is not warranted or desired (such as where spinal stenosis and nerve impingement is not a significant concern), the repair and/or replacement of one or more facet joints can be accomplished in a least-invasive fashion, using one or more cannulae to implant the prosthesis and associated distal hardware. Alternatively, where removal of the facet joints and/or lamina is necessitated, such a procedure can be accomplished through a combination of open, semi-open and/or minimally invasive procedures (which will be referred to herein as a modified-open or mini-open procedure) to minimize damage and/or disruption to surrounding soft-tissue structures. In such a procedure, one or more of the facet joint capsules can be exposed through an open incision (to allow easy resection and removal of the facet joint and/or surrounding anatomical structures), and the components of the dynamic device can be delivered through a cannula or other minimally-invasive delivery method.

Various alternative embodiments of the present invention could incorporate laminar, spinous process, pedicle-based and/or vertebral body fixation elements, or any combinations thereof, ultimately desirous for replacing and/or augmenting the natural facets and other intervertebral tissues. Of course, the systems disclosed herein may be anchored to the vertebral bodies in various ways, including the use of screw threads or stems, with or without using cement and/or bony ingrowth surfaces to augment fixation.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method for stabilizing a spine comprising the steps of:
accessing posterior portions of the spine;
providing a dynamic spine prosthesis comprising:
a fixation element having an elongated bone entry portion defining a longitudinal axis;
a dynamic spine prosthesis component connected to the fixation element at a connection location by an adjustable connection, the adjustable connection comprising first and second washers each rotatably supported by the fixation element and each having an angled contact surface in a plane not perpendicular to the longitudinal axis of the fixation element, the connection location being between the bone entry portion and the first and second washers, wherein the angled contact surfaces of the first and second washers are in contact with each other; and
a third washer between the dynamic spine prosthesis and the bone entry portion of the fixation element, and
positioning the dynamic spine prosthesis on the spine.

2. The method of claim 1, further comprising a tightening element having a first position enabling movement between the first and second washers and the fixation element and a second position preventing movement between the washers and the fixation element.

3. The method of claim 2, wherein the tightening element is a compression nut mounted on a threaded extension of the fixation element.

4. The method of claim 1, wherein the dynamic spine prosthesis component is a facet joint prosthesis comprising an articulation surface configured to articulate with a corresponding facet joint element.

5. The method of claim 1, wherein the third washer comprises a partial spherical surface.

6. The method of claim 1, wherein the adjustable connection comprises a structural attachment element supporting the dynamic spine prosthesis component, the structural attachment element having a first position in which the dynamic spine prosthesis component is movable with respect to the structural element and a second position in which the dynamic spine prosthesis component is fixed with respect to the structural element.

7. The method of claim 1, wherein each of the contact surfaces of the first and second washers is not perpendicular to the axis of the fixation element.

8. The method of claim 1, further comprising rotating the first or second washer about the fixation element to change the angle between a portion of the dynamic spine prosthesis component and the fixation element.

9. The method of claim 1, wherein the fixation element is a cephalad fixation element configured for attaching a first cephalad joint bearing element to a first vertebra.

10. The method of claim 9, further comprising a first crossbar extending from the first cephalad facet joint bearing element to a second cephalad facet joint bearing element.

11. The method of claim 1, further comprising a caudal fixation element configured for attaching a first caudal joint bearing element to a second vertebra.

12. The method of claim 11, further comprising a second crossbar extending from the first caudal facet joint bearing element to a second caudal facet joint bearing element.

13. The method of claim 1, further comprising an arm extending from the fixation element.

14. The method of claim 13, further comprising rotating the first and second washers to adjust an angle between the fixation element and the arm.

15. The method of claim 14, further comprising fixing the angle between the arm relative to the fixation element.

* * * * *